United States Patent [19]

Van Aken et al.

[11] Patent Number: 4,770,530

[45] Date of Patent: Sep. 13, 1988

[54] REMOTE SPECTROPHOTOMETER

[75] Inventors: Harold Van Aken, Callicoon Center; William L. Weber, Walkill, both of N.Y.

[73] Assignee: Kollmorgen Corporation, Simsbury, Conn.

[21] Appl. No.: 855,168

[22] Filed: Apr. 23, 1986

[51] Int. Cl.[4] ............................................. G01J 3/42
[52] U.S. Cl. .................................... 356/323; 356/319; 356/448
[58] Field of Search ............... 356/308, 319, 320, 323, 356/324, 325, 328, 334, 448

[56] References Cited

U.S. PATENT DOCUMENTS

| | | | |
|---|---|---|---|
| 3,446,972 | 5/1969 | Bentley et al. | 356/229 X |
| 3,458,261 | 7/1969 | Bentley et al. | 250/228 X |
| 3,813,172 | 5/1974 | Walker et al. | 356/225 |
| 3,818,198 | 6/1974 | Walker et al. | 356/233 X |
| 3,822,098 | 7/1974 | Rudder et al. | 356/320 |
| 3,891,317 | 6/1975 | Walker | 356/222 X |
| 4,022,534 | 5/1977 | Kishner | 356/446 X |
| 4,076,421 | 2/1978 | Kishner | 356/446 X |
| 4,097,152 | 6/1978 | Kishner | 356/328 |
| 4,449,821 | 5/1984 | Lee | 356/319 |
| 4,529,308 | 7/1985 | Rife | 356/323 |

FOREIGN PATENT DOCUMENTS 58-102114  6/1983  Japan ................................. 356/319

OTHER PUBLICATIONS

Hiraga et al., "Measurements of Spectral Characteristics of Optical Thin Film by Rapid Scanning Spectrophotometer", Japan J. Appl. Phys. Suppl. 2, PT1, 1974, pp. 689-692.

Primary Examiner—Vincent P. McGraw
Attorney, Agent, or Firm—Morgan & Finnegan

[57] ABSTRACT

A spectrophotometer (10) is provided having the capability to accurately measure spectral reflectance at relatively long sample distances. A first illumination optics arrangement (14) assures uniform illumination to a portion of the sample and a second optical arrangement (20) focuses the reflected image of part of the illuminated sample onto a polychromator (22). Reference beam means are provided so that the polychromator sequentially measures the spectral characteristics of the reference beam and the sample. Continuous monitoring of the illumination at select wavelengths provides illumination normalization data so that a microprocessor (40) can normalize the illumination and compare the reference beam and sample measurements to accurately determine the spectral reflectance characteristics of the sample. Angular and raster scanning capability is also provided.

27 Claims, 7 Drawing Sheets

REMOTE SPECTROPHOTOMETER

TECHNICAL FIELD

This invention relates to a remote spectrophotometer for conveniently and accurately measuring the spectral characteristics of a sample at relatively long distances.

BACKGROUND AND OBJECTS OF THE INVENTION

Spectrophotometers are widely used in many settings to determine spectral reflectance. As an industrial quality control tool, spectrophotometers are used to determine whether goods in production are of consistently acceptable appearance. In short, the object is to ensure that the spectral reflectance of the production material is consistent throughout its length and width so that the ultimate goods will be of the highest possible quality. By way of example, textile manufacturers use spectrophotometers during continuous production to monitor the consistency and effectiveness of their dying processes. Ideally, the textile manufacturers would place a spectrophotometer on every final inspection rack to ensure consistent quality of each roll of material at the final production stage prior to shipping. As discussed below, however, limitations of prior spectrophotometers make it impractical for textile manufacturers to mount a spectrophotometer on every inspection rack.

First, previously known spectrophotometers must be mounted in close proximity to the sample being measured, typically within one inch of the production line, in order to eliminate interference from ambient light and obtain a sufficiently intense reflection from the sample. In order to mount prior spectrophotometers in such close proximity to the production material it has been necessary to build expensive bridge mountings which must be custom-designed for each application Secondly, it is often necessary for the spectrophotometer to be able to scan the continuous production sheet. But prior spectrophotometers must be physically transported across the sample in a spatial scan in order to maintain the spectrophotometer in close proximity to the sample. This type of spatial scanning adds considerably to the cost of the bridge mounts since not only must the spectrophotometer be mounted close to the sample, it must be mounted so that it can move across the sample while maintaining its close position. Needless to say, acceptable tolerances for such a scan are difficult to attain in industrial settings. With respect to the textile industry, textile inspection racks are too numerous for installation of a spectrophotometer on each final inspection rack to be economically feasible. Consequently, textile manufacturers have mounted spectrophotometers only on their dying ranges, which are less numerous than the inspection racks. But measurements made at the dying ranges are a less reliable indication of final product quality than measurements taken at the final inspection stage, so accuracy is plainly sacrificed in order to obtain affordability.

Moreover, the need to movably mount prior spectrophotometers close to the sample and the consequent expense of providing custom bridge mountings have prevented the use of spectrophotometers as a quality control tool in some industries. Indeed, many industries have found installing spectrophotometers too costly due to the cost of the bridge mounts to warrant their use. In addition, the requirement that prior spectrophotometers be situated close to the production line has prevented use of spectrophotometers where the sample environment is simply too harsh for the spectrophotometer or where there is simply insufficient room to install a custom bridge mounting. In other situations the specialized nature of the application makes installation of prior spectrophotometers prohibitive. For example, the food industry has not adopted spectrophotometers as a color measurement tool in part because the bridge mountings would have to be constructed from stainless steel in order to satisfy health standards. The high cost of such mounting structures has to date outweighed the advantages of using spectrophotometers in this industry.

As yet a further drawback, prior spectrophotometers positioned close to the sample surface simply cannot accurately measure some surfaces. Prior spectrophotometers include an illumination source which emits light in many directions from a point source and a detector which receives and detects the light reflected from the surface being measured. This arrangement provides an adequate measurement for most continuous flat surfaces when the light source and detector are placed close to the sample, but is unreliable when surfaces having a relief profile are spatially scanned. By way of example, the manufacture of sculptured carpets is one application where accurate spectral measurements would be desirable but have heretofore been unattainable. These carpets have an uneven surface and a traditional spectrophotometer placed close to such a carpet will not give accurate spectral reflectance measurements since each area of the sculptured carpet reflects light in different directions at varying intensities. Consequently, the light reflected to the detector from a sculptured carpet differs widely from area to area as a result of the carpet contour and a scan of this surface with a traditional spectrophotometer will yield erratic and unreliable results. This limitation is largely responsible for the carpet industry's wholesale refusal to use spectrophotometers since carpet manufacturers are reluctant to adopt a quality control tool which can be used on some but not all of their products.

Therefore, it is one object of the present invention to provide a spectrophotometer which may provide highly accurate spectral measurements when operated from relatively great distances to the subject.

It is a further object of the present invention to provide a spectrophotometer which may be operated at relatively great distances from the subject to obtain an accurate measurement without interference from ambient lighting conditions.

It is yet a further object of the present invention to provide a spectrophotometer which may be operated at relatively great distances to the subject without any need for complex bridge mount constructions.

It is a still further object of the present invention to provide a spectrophotometer which may be operated from a stationary point at a relatively great distance to the subject which provides an accurate scan of the subject.

It is a still further object of the present invention to provide a spectrophotometer which may be operated at relatively great distances to the subject without any need to realign or refocus the spectrophotometer should the distance between the spectrophotometer and the sample change.

It is yet another object of the present invention to provide a spectrophotometer which may be operated at relatively great distances to the sample with the illumination source and the detector arranged adjacent to one another, as in a single housing.

These and other highly desirable and unusual results are accomplished by the present invention in a compact structure which performs a quick, accurate scan to determine the spectral reflectance characteristics of a sample.

Objects and advantages of the invention are set forth in part herein and in part will be obvious herefrom, or may be learned by practice with the invention, the same being realized and attained by means of the instrumentalities and combinations pointed out in the appended claims.

The invention consists in the novel parts, constructions, arrangements, combinations, steps, and improvements herein shown and described.

SUMMARY OF THE INVENTION

In accordance with the present invention, a spectrophotometer is provided which provides accurate spectral reflectance measurements at relatively great distances. Scanning capability is also provided.

In the first preferred embodiment a high intensity illumination source, preferably a pulsed Xenon lamp, is provided. An illumination focusing lens focuses a magnified image of the source or, alternatively, projects a collimated beam from the source onto an area of the sample to be measured. One end of at least one reference fiber optic members is positioned in the path of the illumination to obtain a reference beam for comparison purposes. The other end of the fiber optic member is butted against a bandpass filter adjacent to a reference detector.

A sample imaging lens is aligned to view a portion of the illuminated sample area and focuses the image onto a polychromator positioned so that the light reflected from the sample is separated into its component wavelengths for separate detection by an array of detectors. The detected sample illumination and reference beams are amplified and converted into digital signals for processing by a microprocessor. The microprocessor determines the spectral reflectance of the sample using the reference beam information as a basis for determining the characteristics of the sample illumination. Advantageously, the reflected sample illumination is averaged over a relatively large sample area.

In the second preferred embodiment a Kohler type illumination optics system similar to the illumination systems used in film projectors is provided. In this embodiment the illumination from the preferred pulsed Xenon lamp is incident upon a condenser lens and passes through an aperture to an objective lens. The objective lens focuses an image of the aperture onto an area of the sample to provide uniform sample illumination. A beamsplitter is placed between the condenser lens and the objective lens to obtain an illumination reference beam. The reference beam is focused onto the distant wall of an integrating sphere coated on its inner surface with uniform white coating to produce an integrated diffuse reference source.

In this embodiment the optical path from the illuminated area of the sample to the sample imaging lens passes through or alongside the integrating sphere. A beamswitch is provided which sequentially directs the integrated reference beam, as imaged on the inner surface of the integrating sphere, and the reflected sample image onto the polychromator during two sequential flashes of the preferred pulsed Xenon lamp. One or more discrete wavelength detectors, preferably consisting of an optical fiber connected to a bandpass filter and a reference detector, are associated with the integrating sphere to monitor the spectral characteristics of the illumination source during both the reference and sample flashes.

In the second preferred embodiment the microprocessor normalizes the illumination source between the two flashes utilizing the information obtained from the discrete wavelength detectors and then compares the sample and reference measurements on the basis of the normalized illumination. From this comparison the spectral reflectance characteristics of the sample are determined. Advantageously, the illumination and sample fields of view overlap to provide a relatively long depth of view once the system is aligned. Since the sample illumination is very uniform, this system is able to provide accurate spectral reflectance measurements over a long depth of field without realignment or recalibration. By sampling a relatively large, uniformly illuminated surface area the present invention provides accurate spectral reflectance measurements which are less dependent upon surface variations than prior spectrophotometers.

Alternative configurations of the second preferred embodiment are provided. In one such configuration a second polychromator is provided to receive and comprehensively analyze the spectral characteristics from the discrete wavelength detectors. In a further variation involving dual polychromators, the reference beam is focused directly onto a second polychromator without any integrating sphere.

In another configuration the reference beam is projected onto a diffuser by a conjugate objective lens and the beamswitch alternately directs the diffuse reference illumination from the diffuser or the reflected sample image to the polychromator. In this configuration the discrete wavelength detectors for providing a normalization reference preferably constitute fibers disposed in the path of the diffuse illumination.

Other variations include an integrating rod as part of the illumination optics and a flyback scanning mirror to provide an angular and/or raster scanning spectrophotometer.

It will be apparent from the foregoing general description that the objects of the invention specifically enumerated herein are accomplished by the invention as here embodied.

Thus, as one advantage of the present invention a spectrophotometer is provided which remarkably permits the spectral reflectance of the sample to be measured at a relatively great distance to the sample. Advantageously, this permits the spectrophotometer according to the present invention to be mounted away from the sample without any need for expensive bridge mountings.

It will also be apparent that the ability of the present spectrophotometer to measure spectral reflectance at a distance to the sample allows the spectrophotometer to be removed from the immediate industrial processing environment of the sample, as by placing the spectrophotometer behind a clear glass barrier away from the production line.

As a further advantage of the invention the present spectrophotometer is able to accurately average the measurement of a uniformly illuminated sample area to advantageously reduce inaccuracies which might otherwise result from measuring a localized area of an irregularly contoured surface.

As yet a further advantage of the present invention remarkably accurate measurement of the spectral reflectance of a sample is provided using a dual beam comparison technique.

As a still further advantage of the present invention accurate angular scanning is remarkably obtained from a stationary point of view at a distance to the sample.

It will be understood that the foregoing general description and the following detailed description as well are exemplary and explanatory of the invention but are not restrictive thereof.

BRIEF DESCRIPTION OF THE DRAWINGS

The accompanying drawings, referred to herein and constituting a part hereof, illustrate preferred embodiments of the product of the present invention, and together with the description serve to explain the principles of the invention, in which.

DETAILED DESCRIPTION OF THE PREFERRED EMBODIMENTS

Figure 1:
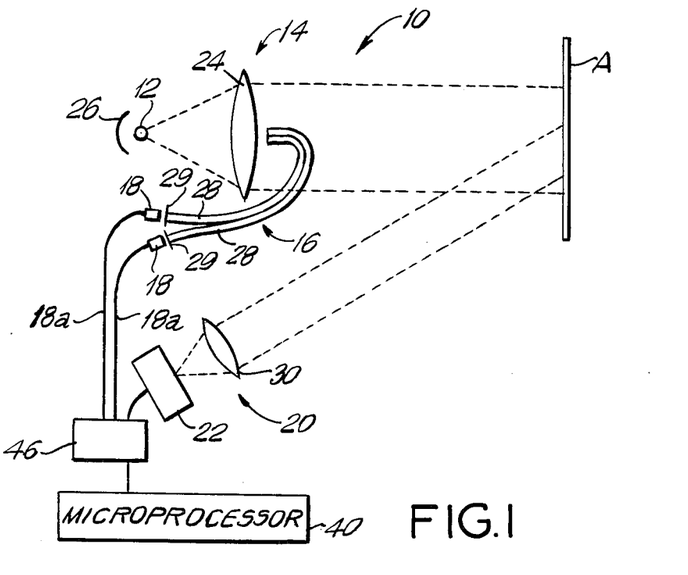
FIG. 1 is a plan view of a remote reading spectrophotometer in accordance with the first preferred embodiment of the present invention.

Referring now to the drawings, which have common reference numerals corresponding to like elements, a spectrophotometer generally shown as 10 is provided having an illumination source 12, a first optical arrangement 14 consisting of one or more lenses, reference beam means 16 to carry a reference beam to one or more reference detectors 18, a second, reflected light optical arrangement 20 to focus the illumination reflected from a sample A onto a polychromator 22 which separates and detects the intensity of the reflected sample illumination at numerous wavelengths, amplifying and integrating circuitry 46, and a microprocessor 40 to receive and process the data generated by the polychromator and reference detectors for further use in data display and/or system control In the first preferred embodiment of the invention shown in FIG. 1 illumination source 12, preferably a high intensity pulsed Xenon lamp or continuous Xenon arc lamp, projects light to a focusing lens 24. As shown, a curved polished reflector 26 may be disposed behind lamp 12 to ensure that as much light as possible is directed toward focusing lens 24 and to minimize the effects of beam drift or arc wander. Preferably, polished reflector 26 is a spherical mirror with a magnification factor of minus one.

Focusing lens 24 projects the illumination from light source 12 toward the sample A so as to illuminate a portion thereof. Focusing lens 24 may either focus the illumination onto the sample as a magnified image of the illumination lamp or project the light in a collimated beam, as shown in FIG. 1, to create a defocused spot on the sample. In either case, an area of the sample is illuminated. One or more fiber optic pick-ups 28 are disposed in the path of the sample illumination to provide a reference beam of the illumination projected toward sample A. The reference beams from fiber optic elements 28 are filtered through bandpass filters 29 and are incident upon reference beam detectors 18, as by butting the end of each optical fiber against the filter and detector pair. The filters might have a bandwidth on the order of thirty nanometers so that reference measurements at roughly two select wavelengths are obtained. Alternatively, the reference beam may be obtained using traditional optical elements, such as a beamsplitter and a focusing lens.

Sample A responds to the incident light by reflecting and absorbing different amounts of light at each wavelength to define the spectral "fingerprint" of the sample. A second optical arrangement 20, shown in FIG. 1 as a reflected light focusing lens 30, is provided to receive light reflected from a portion of the illuminated area of sample A and focus that reflected light onto a polychromator 22, where the reflected light is broken down into its component wavelengths for detection.

Figure 2:
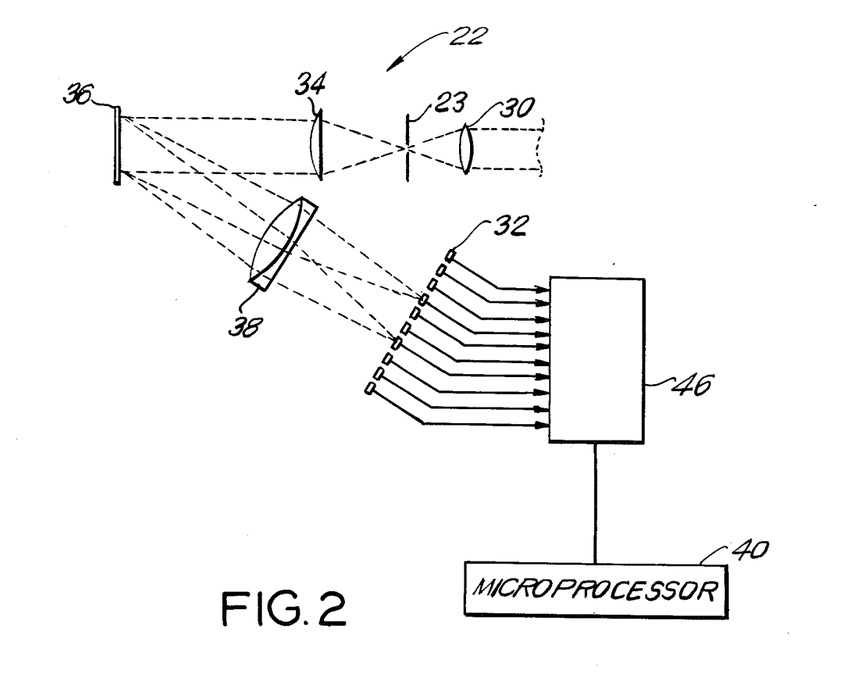
FIG. 2 is a plan view of a first suitable polychromator and analysis circuit in accordance the present invention.

. A suitable polychromator arrangement is shown in FIG. 2. As there shown, polychromator 22 includes a narrow slit 23 placed at the focal point of lens 30, a collimating lens 34, a dispersive element 36 such as a diffraction grating or a prism which receives the collimated beam from collimating lens 34 and separates the beam into its component wavelengths, and a focusing lens 38 which focuses the separated light from the dispersive element onto a detector array 32. Detector array 32 includes detectors positioned to receive incident light corresponding to each wavelength region, thereby providing a multiple channel detection system. For convenience, detector array 32 is shown as an array of ten detectors to provide a ten channel system. It is preferred, however, to provide a twenty or forty channel system to detect light at twenty or ten nanometer intervals, respectively, throughout the visible spectrum. It is also contemplated that the present spectrophotometer might find application in non-visible regions of the spectrum. A polychromator arrangement as described herein is shown and described in U.S. Pat. No. 4,076,421 issued to Kishner for "Spectrophotometer with Parallel Sensing."

Processing circuitry 46 receives the signals from each detector of array 32 for processing in an appropriate manner. This processing may involve amplification and integration of the signals for transmission to microprocessor 40. Needless to say, an analog to digital converter must be included, preferably within the microprocessor, in order for the microprocessor to receive and understand the amplified analog detector signals.

Figure 3:
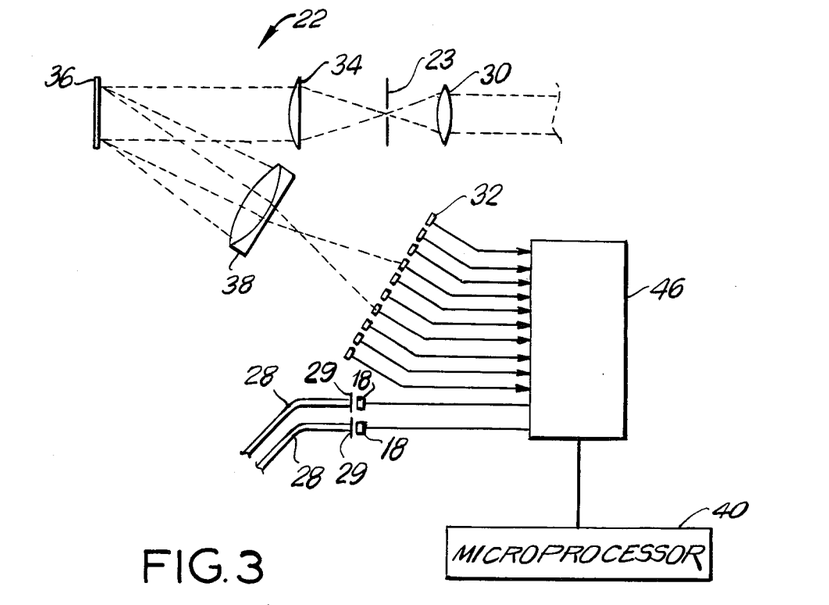
FIG. 3 is a plan view of a second suitable polychromator and analysis circuit including fiber optic reference beam leads connected directly to the polychromator.

FIG. 3 shows an alternative arrangement for polychromator 22. There, fiber optic members 28 are led directly into the polychromator where dedicated filters 29 and reference detectors 18 are provided. It is contemplated that reference detectors 18 may simply be an extension of detector array 32.

Although the polychromator arrangements described above and shown in FIGS. 2 and 3 are preferred, other polychromator arrangements may be suitable and, indeed, even a monochromator arrangement may be used. Thus, the individual wavelengths of the reflected sample illumination to be measured may be sequentially directed to a single detector by adjusting the color separation device. As in the preferred polychromator arrangement, the single detector signal would then be relayed to the amplifying and microprocessing circuitry.

Preferably, the analog to digital converter is included within microprocessor 40, which receives and stores the data from the reference detectors and the sample detector array 32. The reference detector data is used to normalize the sample illumination to account for any shifts which may have occurred since the instrument was calibrated and the sample measurement is then processed to calculate the spectral characteristics of the sample. The microprocessor may then provide a display of sample's spectral characteristics, i.e. the degree of reflectance of the sample at each measured wavelength, and/or automatically make process control adjustments based upon the sample measurements.

As previously stated, the preferred illumination source is a high intensity pulsed Xenon lamp. Use of this readily available source with the dual beam measuring technique of the present invention advantageously permits ambient room light to be ignored. Moreover, heretofore unknown accuracy is obtained since the characteristics of the incident as well as reflected illumination are measured by the present invention. Consequently, the spectrophotometer according to the present invention can be used in room light at relatively long distances without any interference from ambient light. Indeed, the present invention permits accurate spectral reflectance measurement at distances on the order of four to twenty feet. Of course, it is also contemplated that appropriate sources other than the preferred pulsed Xenon lamp may be used. For example, a high intensity pulsed Krypton lamp or other pulsed noble gas lamp may be appropriate. It is also believed that a continuous source such as an arc lamp which provides high intensity illumination or a light source modulated to frequencies above room light could be used.

The optical configuration shown in FIG. 1 and described above has been found acceptable for numerous applications and may be applied with success, but certain limitations of that particular configuration have led the inventors to devise improvements which permit even greater accuracy and reliability in spectral measurements at long distances.

In particular, since the illuminated spot on the sample is a direct image of the lamp source it has been found that the preferred Xenon illumination may vary over a small area of the illuminated spot depending upon the location of lamp's "hot spots" in the image. Since lamp sources and, more particularly, the preferred Xenon lamp, often suffer from single beam drift or arc wander, the illumination at the sample can vary even without adjustment of the optics or movement of the sample. The effects of variations in the illumination at the relatively small reference beam pick-ups 28 disposed in the illumination path can be even more pronounced. Where, as here, it is desired to operate the system at various sample distances and in situations where the sample position might vary somewhat during measurement, inconsistent illumination can lead to inaccuracies and a lack of repeatability. The curved mirror disposed behind light source 12 helps reduce the effects of beam drift and arc wander, but complete uniformity is not obtained with this improvement alone.

In addition, the structure shown in FIG. 1 must be refocused and the non-uniform light source must be re-calibrated if the sample distance changes. Since the illumination at the sample is not very uniform, the working range is limited to a relatively shallow depth of focus surrounding the actual focal point. Although these limitations of the first preferred embodiment may be overcome by closely monitoring the system, greater versatility and reliability is desirable.

Therefore, further embodiments of the present invention have been developed to overcome these and other drawbacks of the first preferred embodiment illustrated in FIG. 1.

Figure 4:
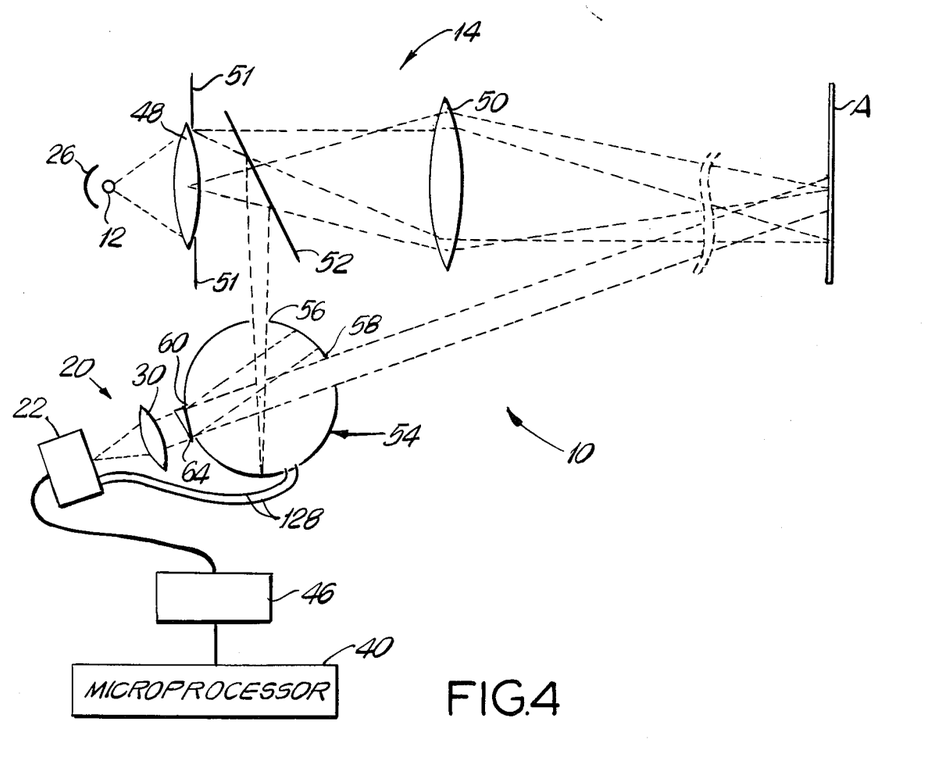
FIG. 4 is a plan view of a remote reading spectrophotometer in accordance with the second preferred embodiment of the present invention.

Referring now to FIG. 4, having common reference numerals corresponding to like elements of FIGS. 1 through 3, a second preferred embodiment of the present invention including a Kohler type optical arrangement to assure uniform illumination at the sample is shown.

In this embodiment the preferred pulsed Xenon light source 12 is provided with a curved reflector 26 to maximize the illumination directed to a first illumination lens 48 and reduce the effects of beam drift. Aperture defining means 51, such as an aperture defining plate, are provided adjacent to first lens 48 to define a distinct illumination aperture. Lens 48 is preferably a condenser lens aligned to focus the illumination from light source 12 onto an objective lens 50, which focuses an image of the aperture onto the sample. Since objective lens 50 focuses an image of the aperture rather than of the light source itself onto the sample the illumination at the sample is highly uniform. Advantageously, objective lens 50 compensates for any slight variations in light source 12 so that the illuminated area of sample A remains steady.

Thus, the illumination optics of the second preferred embodiment provides a uniformly illuminated spot on the sample. This facilitates proper alignment of the illumination and detection optics to assure an overlapping field of view and, consequently, accurate detection of the reflected illumination.

In this second preferred embodiment the reference beam is obtained by providing a beamsplitter 52 between first and second lens elements 48 and 50, respectively. Beamsplitter 52 reflects a portion of the sample illumination from first lens 48 to an integrating sphere 54 through a first integrating sphere aperture 56. Preferably, the reference beam is focused at a point on the far wall of the integrating sphere from opening 56 and the inner walls of integrating sphere 54 are coated with a uniform white coating so that the entire sphere becomes illuminated with a diffuse image of the reference beam.

Integrating sphere 54 is also provided with second and third integrating sphere apertures 58 and 60, respectively. The reflected sample beam from a portion of the illuminated area of sample A passes through integrating sphere 54 along the chord defined by apertures 58, 60 to sample focusing lens 30, which focuses the beam onto polychromator 22. As in the first preferred embodiment, the sample beam is detected by detector array 32, processed by amplifying and integrating circuitry 46, and sent to microprocessor 40 so that the information can be translated into useful numerical data corresponding to the spectral reflectance characteristics of sample A.

Advantageously, a beamswitch 64 is provided adjacent to third integrating sphere aperture 60. In one position the beamswitch permits unobstructed viewing of the sample beam by focusing lens 30 and in another position a reference beam from a portion of the white wall of integrating sphere 54 is directed to focusing lens 30 to the exclusion of the reflected sample image. In this manner beamswitch 64, which may for example be a pivoting prism, permits either the integrated reference beam or the sample beam to be selectively viewed by sample focusing lens 30 and, consequently, polychromator 22. As a practical matter, when the preferred pulsed Xenon lamp is used as illumination source 12, two sequential pulsed flashes are provided. During one flash beamswitch 64 directs the sample beam to focusing lens 30 to be detected by polychromator 22 The spectral information from the sample is detected during this flash and is stored by microprocessor 40. During the second flash beamswitch 64 alters the line of sight of focusing lens 30 to a portion of the inside wall of integrating sphere 54 so that the integrated reference beam is focused onto polychromator 22. The spectral information from the reference flash is also stored by microprocessor 40. Thus, after both flashes are complete microprocessor 40 has stored in it the full spectral characteristics of both the reference beam and the sample beam. Consequently, the data obtained from the sample beam can be analyzed relative to the reference beam data to determine the spectral characteristics of the Sample A.

It has also been found desirable to provide one or more discrete reference beam optical pick-ups 128, such as optical fibers, within the integrating sphere to monitor the illumination at one or more wavelengths during both flashes in a manner similar to the function of reference beam fibers 28 of the first preferred embodiment shown in FIG. 1. Thus, two fiber optic pick-ups 128 are preferably led from integrating sphere 54 directly into polychromator 22, where they connect to bandpass filters 29 and dedicated reference detectors 18 (see FIG. 3). It has been found that this type of measurement during both flashes at just two wavelengths, such as approximately 440 and 620 nanometers, can be correlated to give a reliable indication of shifts or failures in the illumination source For more demanding applications the measurements at these select wavelengths can be correlated to indicate changes at other wavelengths so that the reference and sample flashes can be normalized to provide a more accurate comparison of the reference beam and sample image measurements.

Figure 5A:
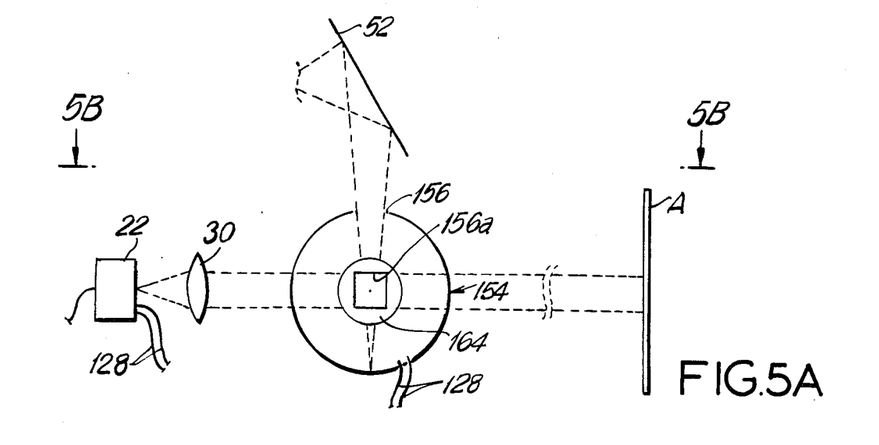
FIG. 5A is partial plan view of the second preferred embodiment of the present invention illustrating an alternative integrating sphere configuration.
Figure 5B:
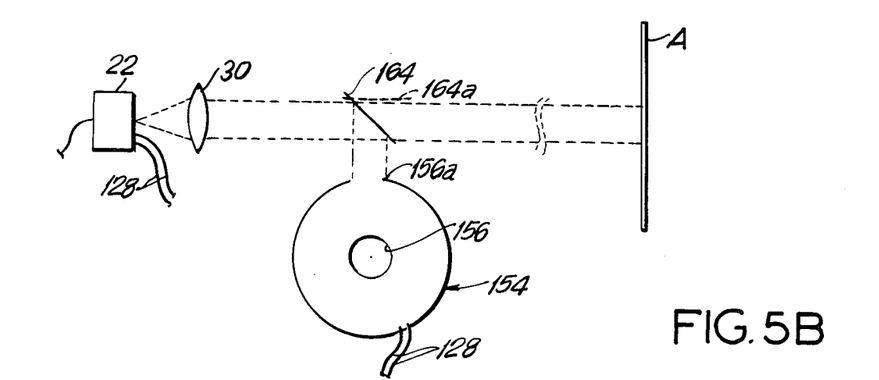
FIG. 5B is a side view of the alternative integrating sphere configuration illustrated in 5A, taken along line 5B—5B of FIG. 5A.

It is also contemplated, of course, that the sample beam might not pass through integrating sphere 54. One suitable configuration of the spectrophotometer according to the present invention in which the sample beam does not pass through the integrating sphere is shown in FIGS. 5A and 5B. FIG. 5A, a side view of this alternative configuration, shows the reference beam from beamsplitter 52 reflected into integrating sphere 154 through aperture 156. In this arrangement the sample beam passes alongside the integrating sphere adjacent to the reference aperture 156a. FIG. 5B, a top partial view of the structure shown in FIG. 5A taken along line 5B—5B, clearly shows that beamswitch 164 alternates between the position shown wherein the reference beam from integrating sphere 154 is directed to focusing lens 30 and position 164a, shown in phantom, out of the path of the sample beam, such that the sample beam is directed to focusing lens 30 to the exclusion of the reference beam. Consequently, polychromator 22 alternately receives and detects light from the reference and sample beams. As in the embodiment shown in FIG. 4, fiber optic pick-ups 128 provide a partial reference at select wavelengths during both flashes.

Figure 5C:
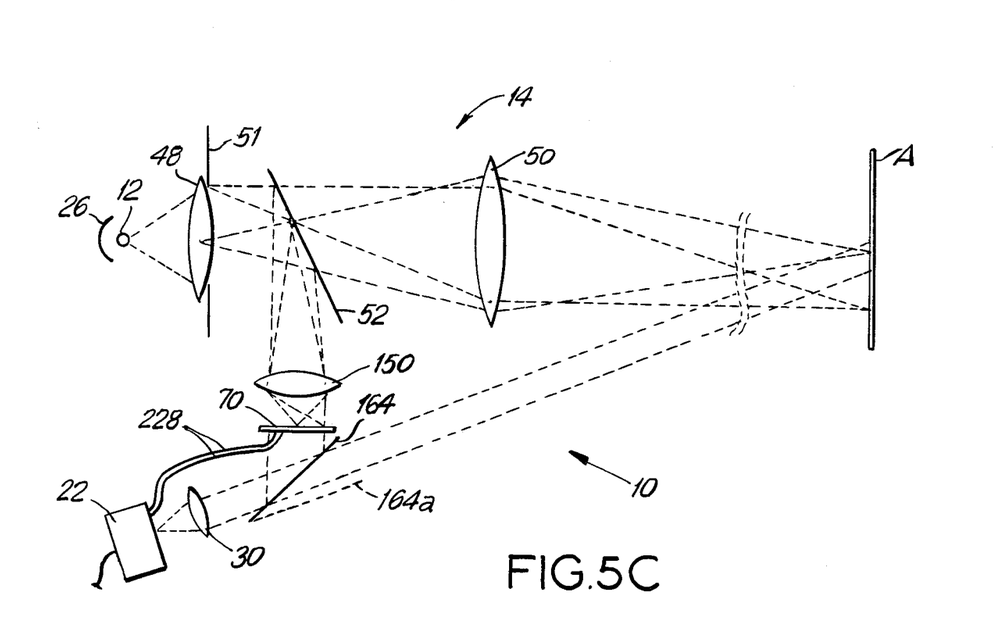
FIG. 5C is a partial plan view of the second preferred embodiment of the invention illustrating a first alternative reference beam optical configuration.

Alternatively, it is also contemplated that the integrating sphere might be replaced by another suitable optical arrangement which provides a uniform averaging of the reference beam. One such arrangement is illustrated in FIG. 5C. There, the reference beam from beamsplitter 52 is focused by a conjugate objective lens 150 similar to the sample illumination objective lens 50 onto a diffuser 70. Beamswitch 164 selectively directs either the sample beam (position 164a) or the diffuse reference beam (position 164) to focusing lens 30 and polychromator 22. In this configuration fiber optic pick-ups 228 would be placed in the path of the reference beam illumination from diffuser 70 in a manner similar to the placement of optical fibers 28 the first preferred embodiment shown in FIG. 1. However, optical fibers 228 are not subject to the illumination variations experienced by fibers 28 since fibers 228 are disposed in the path of uniform diffuse illumination rather than the image of the lamp source as in the first preferred embodiment.

Figure 6:
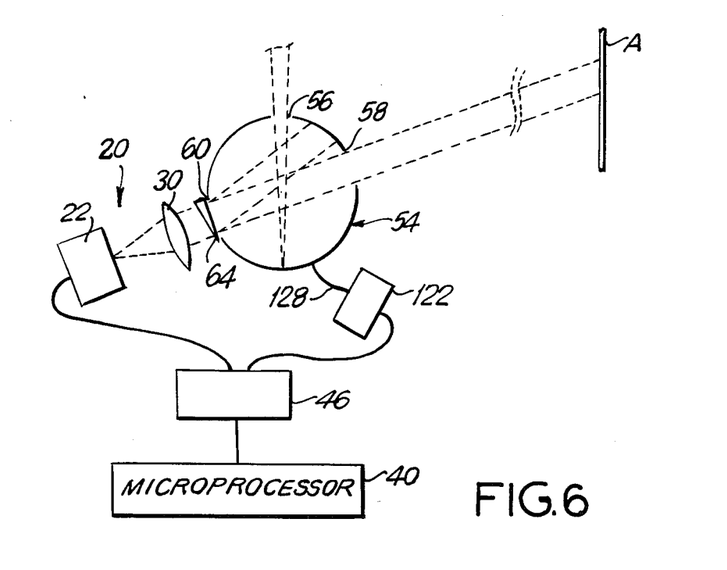
FIG. 6 is a partial plan view of the second preferred embodiment of the invention including dual polychromators.

It is also contemplated that a fiber optic pick-up 128 of the second preferred embodiment (see FIG. 4) could be connected to a second polychromator 122, as shown in FIG. 6, in order to monitor the full reference beam over all pertinent wavelengths during both the reference and sample beam flashes. As shown in FIG. 6, both polychromators could be connected to similar analyzing circuitry. This particular arrangement is desirable since a complete evaluation of the illumination source at all pertinent wavelengths would be obtained during both the reference and sample flashes. Thus, any shift in the illumination source would be known from second polychromator 122 and could be used to correlate the reference and sample beams to give a very accurate indication of the spectral reflectance of the sample.

Figure 7:
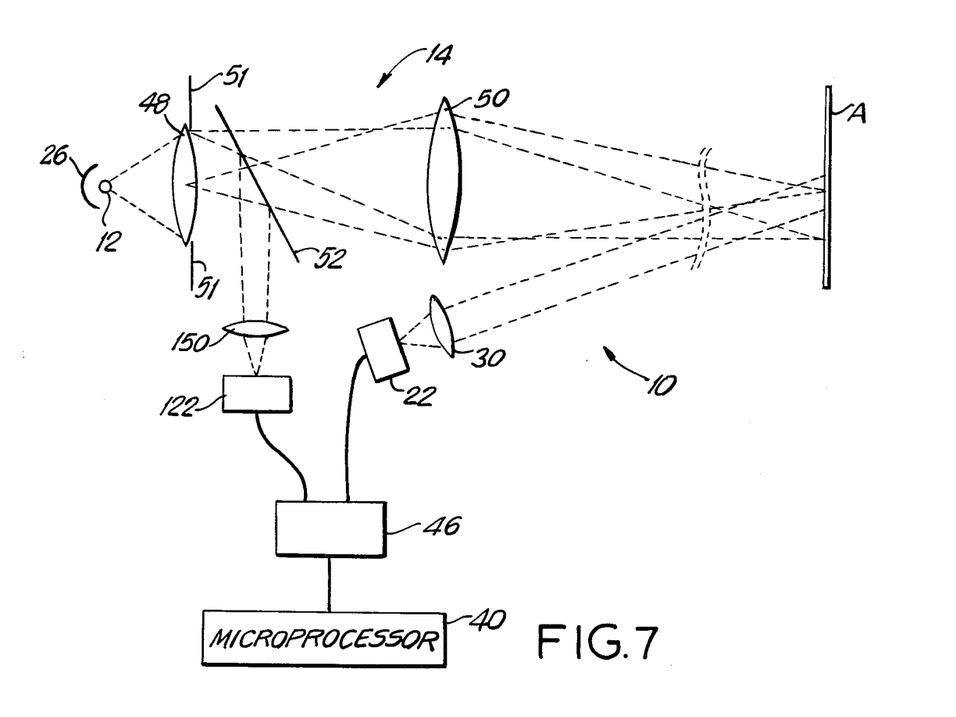
FIG. 7 is a plan view of the second preferred embodiment of the invention including dual polychromators and illustrating a second alternative reference beam optical configuration.

In a further extension of this dual polychromator configuration shown in FIG. 7, reference and sample beams could be measured simultaneously by two polychromators during a single flash of the preferred pulsed Xenon lamp. As there shown, the reference beam is reflected from beamsplitter 52 to a focusing lens 150 and is focused onto second polychromator 122 in order to simulate the sample illumination. As in the configuration shown in FIG. 6, the data from both polychromators 22, 122 could be processed by similar amplifying and integrating circuitry 46 and microprocessor 40. Of course, the disadvantage of the configuration shown in FIG. 7 is that the first and second polychromators 22, 122 should be accurately calibrated relative to one another so that differences between the detection characteristics of the polychromators do not skew the evaluation of the sample reflectance.

Figure 8:
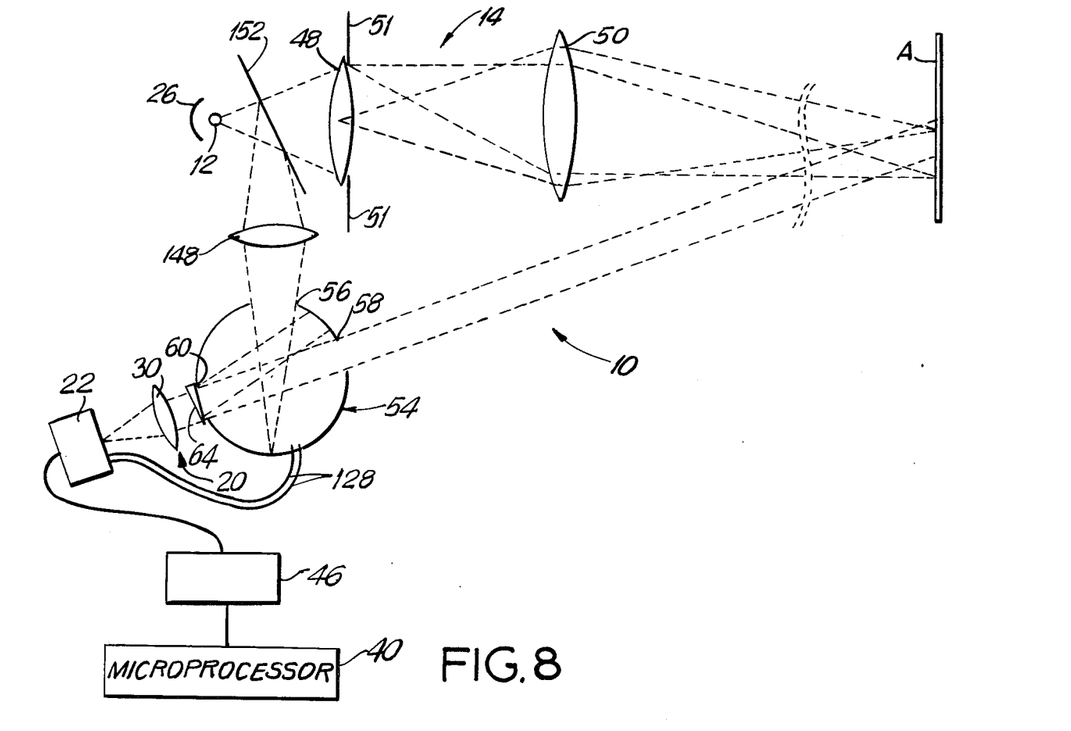
FIG. 8 is a plan view of the second preferred embodiment of the invention illustrating a third alternative optical configuration including conjugate reference beam optics.

A further alternative configuration of the second preferred embodiment of the present invention is shown in FIG. 8. In this configuration the reference beam is obtained by placing a beamsplitter 152 between light source 12 and first lens element 48. Beamsplitter 152 reflects some of the illumination from lamp 12 to a conjugate lens element 148, which focuses the illumination onto the far wall of integrating sphere 54 through aperture 56. As in the configuration of the second preferred embodiment shown in FIG. 4, the sample beam passes through the integrating sphere through second and third apertures 58, 60 and is focused onto polychromator 22 by focusing lens 30. Likewise, beamswitch 64 permits both the sample and reference beams to be measured and integrating sphere optical pick-ups 128 permit the illumination from both flashes to be monitored at select wavelengths.

Of course, the conjugate reference beam optical configuration shown in FIG. 8 could be combined with a dual polychromator system (see FIG. 7) or with a diffuser type system (see FIG. 5C) rather than an integrating sphere.

Figure 9A:
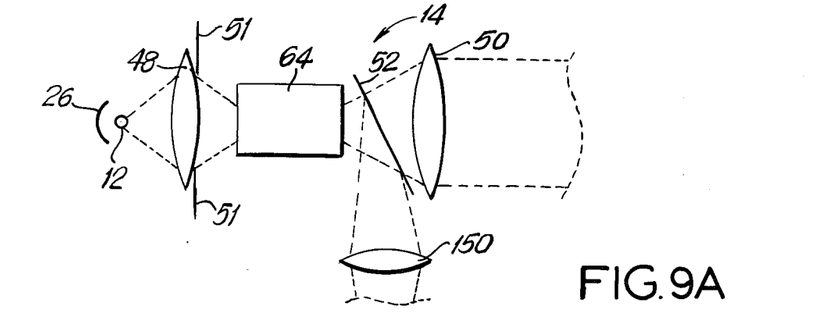
FIG. 9A is a partial plan view of the second preferred embodiment of the invention illustrating a fourth alternative optical configuration including an integrating rod as part of the illumination optics.
Figure 9B:
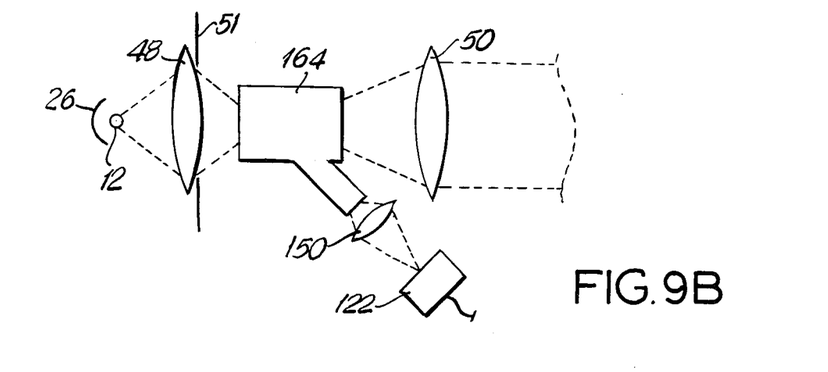
FIG. 9B is a partial plan view of the second preferred embodiment illustrating a fifth alternative optical configuration including a split integrating rod as part of the illumination optics.

It is also contemplated that the first illumination optical arrangement 14 may include an integrating rod such as a fiber optic bundle. Configurations of first optical arrangements including integrating rods are shown in FIGS. 9A and 9B. In FIG. 9A an illumination system according to the present invention including an integrating rod 64 is illustrated. The integrating rod ensures that the illumination from first lens element 48 is accurately projected onto second lens element 50 to further assure uniform sample illumination. Beamsplitter 52 is positioned between integrating rod 64 and second lens element 50, as shown, to project the reference beam onto a conjugate second lens element 150 in a manner similar to the reference beam arrangement shown in FIG. 8. Of course, lens 50 could focus an image of the end of integrating rod 64 onto the sample or a Kohler optical arrangement could be provided in place of lens 50 for even greater uniformity.

An alternative illumination optics arrangement including an integrating rod 164 is shown in FIG. 9B. As there shown, integrating rod 164 could be split to provide the sample and reference beams so that the illumination from lamp 12 enters integrating rod 164 from first lens element 48 and is split to provide both appropriate illumination of second lens element 50 and the reference beam. The reference beam from integrating rod 164 can, for example, be imaged through a conjugate objective lens 150 onto a second polychromator in a similar manner as described in relation to the configuation shown in FIG. 7. Of course, the reference branch of the split integrating rod 164 could be coupled with other reference beam illumination systems shown herein. It is readily apparent that this arrangement is particularly suited to fiber optics technology.

Figure 10:
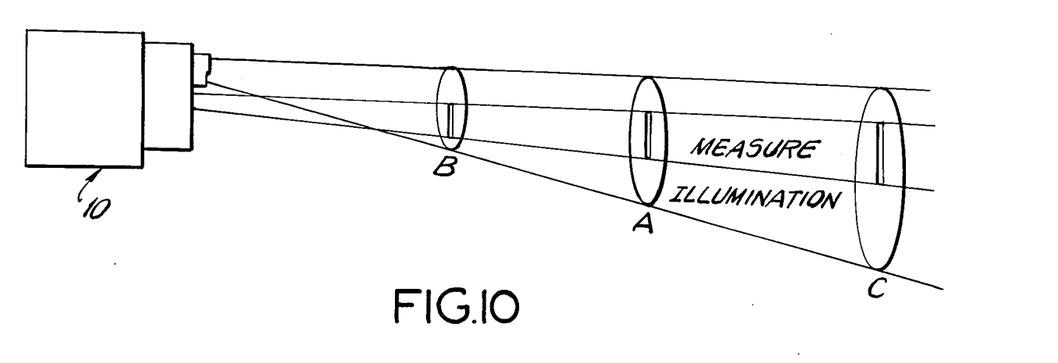
FIG. 10 is a plan view of the second preferred embodiment of the present invention illustrating the overlapping illumination and measurement fields of view.

The second preferred embodiment of this invention provides remarkably uniform illumination at the sample which is, for the most part, independent of the spectrophotometer to sample distance. As illustrated in FIG. 10, since the angle subtended between the illumination beam and the reflected sample image is substantially zero the illumination and measurement fields of view overlap for a relatively great distance to provide a very long depth of field. Thus, when spectrophotometer 10 is calibrated so that the optimum measurement distance corresponds to position A, the measurement field of view fully overlaps the projected illumination at positions B and C as well. By way of example, if the present system in accordance with the second preferred embodiment is aligned for a sample distance of approximately nine feet the depth of view of the system is from approximately four feet to infinity, i.e. the illumination lens has a hyperfocal distance of nine feet. Since this system provides uniform illumination the measurement variations experienced with the first embodiment of the invention due to the various locations of lamp source "hot spots" in the illuminated area are eliminated. Moreover, averaging over a portion of the illuminated area of the sample surface can be achieved with the result that the only distance limitation on the system according to the second preferred embodiment is the brightness level of the illumination source.

Furthermore, the relatively large sample area viewed by the present system according to the second preferred embodiment provides more accurate measurement of the spectral reflectance of the sample since the measurement constitutes an integration over the entire area within the sample field of view. Since sample surfaces actually vary from one area to another this averaging effect contributes to the outstanding accuracy of the present system compared to prior close measurement spectrophotometers. Indeed, the localized measurement used by prior spectrophotometers is partially responsible for the inability of traditional spectrophotometers to penetrate the market for measuring relief surfaces such as sculptured carpets. With prior spectrophotometers the contour variations in sculptured carpet result in dramatic changes in the relative distance from the illumination and pickup members to the sample. This causes wide detection variations. The present invention, on the other hand, permits the spectral characteristics of irregular surfaces to be accurately measured from a distance by taking an overview of a relatively large sample area and averaging the results to accurately determine spectral response. Consequently, any variation in the relative distance from the illumination and detection members to the sample is minimal and any resulting measurement variations are inconsequential.

In sum, the present invention advantageously combines the ability to measure spectral reflectance characteristics at a relatively long distance with a long depth of focus and large sample area averaging. This unique combination of features permits the present spectrophotometer to be mounted away from the sample surface. Accordingly, the present spectrophotometer is inexpensive to install compared to prior spectrophotometers since the need for expensive custom-designed bridge mountings is eliminated. Indeed, by providing spectral measurement from a distance to the sample the present invention can be used in applications where prior spectrophotometers cannot even be considered.

Figure 11:
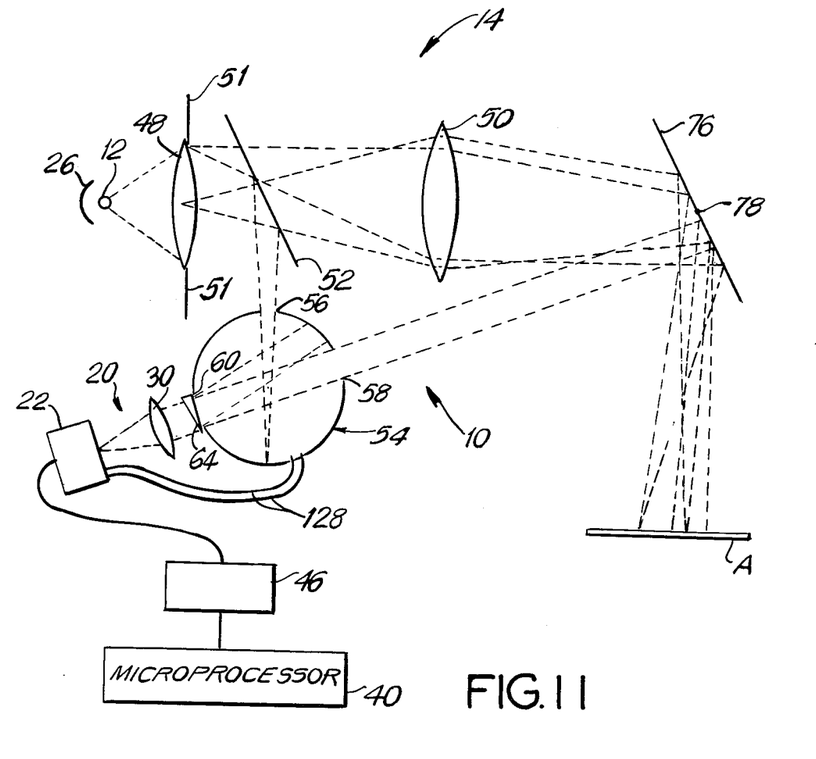
FIG. 11 is a plan view of the second preferred embodiment of the invention including a scanning apparatus.

Furthermore, the unique features of the present invention are particularly adapted for providing an inexpensive angular scanning system since the illumination and detection optical paths subtend a narrow angle. As a result, the respective optical apertures can be placed closely adjacent to one another. As shown in FIG. 11, the spectrophotometer according to the second preferred embodiment of the present invention (see FIG. 4) can be arranged in a scanning configuration by providing a scanning mirror 76 pivotally mounted at center point 78. Preferably, scanning mirror 76 is driven in a "flyback" or "sawtooth" pattern to accomplish an angular scan across sample A. As shown, the illumination beam is reflected to sample A and the corresponding reflected sample beam remains within the measurement field of view. It is also contemplated that a raster scan could be provided either by pivoting scanning mirror 76 in two directions or by providing a second scanning mirror in a known manner.

Figure 12:
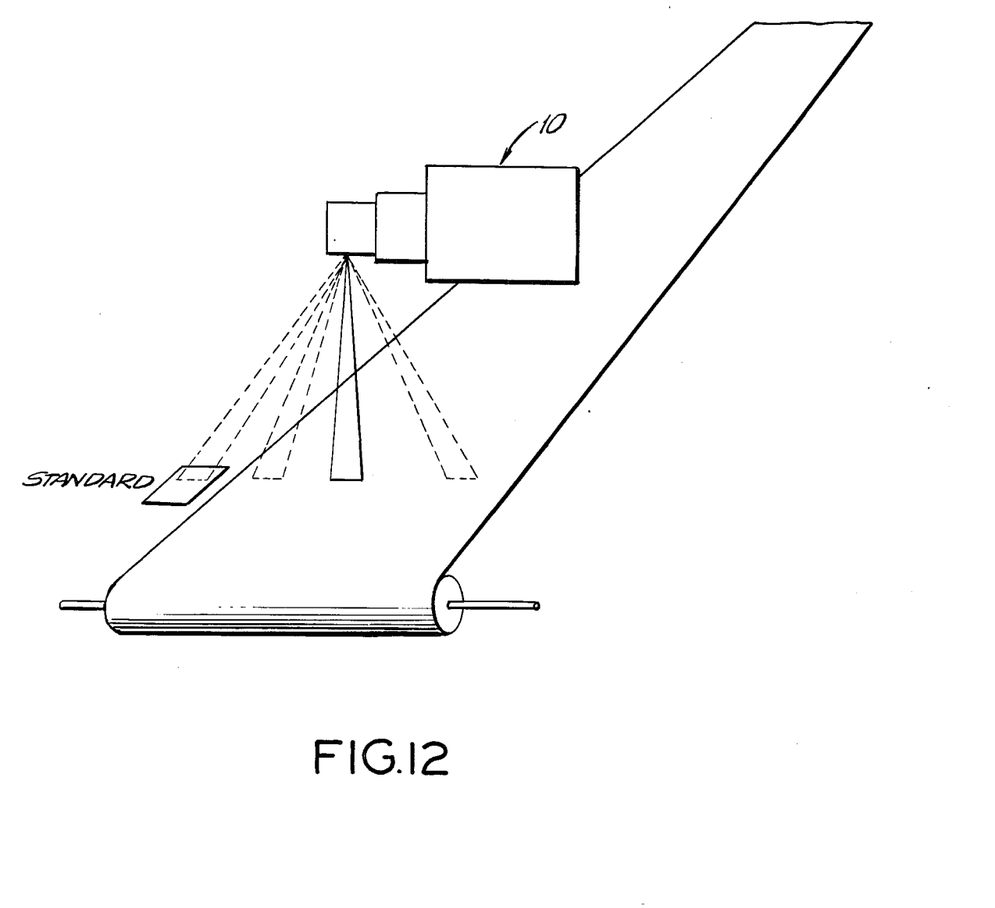
FIG. 12 is a perspective view of a commercial application of the scanning spectrophotometer illustrated in FIG. 11.

A commercial application of the scanning spectrophotometer according to FIG. 11 is illustrated in FIG. 12. As there shown, the scanning spectrophotometer is mounted high above the continuous production sheet material and performs an angular scan across the entire width of the continuous sheet during the pivoting movement of scanning mirror 76 (see FIG. 11). Advantageously, a calibrated measurement standard can be placed adjacent to the production sheet so that the standard is regularly included in the scanning sweep of spectrophotometer 10.

In use, the spectrophotometer according to the present invention is mounted at a fixed location away from the sample to be measured. The illumination and measurement optics are aligned at an appropriate median sample distance and a known calibration standard is placed at the sample location. The spectrophotometer is then calibrated based on this standard and may thereafter be used to measure the spectral reflectance of a sample It is also contemplated that for the scanning spectrophotometer calibration standards corresponding to various points of scan, e.g. left, right and center, be provided to calibrate the scanning spectrophotometer to compensate for any angular color variations introduced by the different scan angles. Of course, the spectrophotometer should periodically be recalibrated using the known standard to ensure accuracy To the extent not already indicated, it also will be understood by those of ordinary skill in the art that any one of the various specific embodiments herein described and illustrated may be further modified to incorporate features shown in other of the specific embodiments, as desired. It will readily be appreciated, for example, that reflective optical elements could be substituted for one or more of the lenses described herein, particularly if non-visual sensing is to be accomplished.

The invention in its broader aspects therefore is not limited to the specific embodiments herein shown and described but departures may be made therefrom within the scope of the accompanying claims, without departing from the principles of the invention and without sacrificing its chief advantages.

What is claimed is:

1. A remote reading spectrophotometer comprising:
   high intensity broadband illumination means;
   first optical means for directing illumination from said illumination means to a relatively large area of a sample to be measured, the sample being disposed at a distance from the spectrophotometer, said first optical means including
     condenser lens means for receiving and transferring illumination from said illumination means,
     aperture defining means adjacent said condenser lens means, and
     objective lens means for transmitting an image of illumination from said aperture defining means onto said relatively large and distant sample area;
   reference beam means disposed in the optical path of said illumination between said aperture defining means and said objective lens means for obtaining an illumination reference beam from said first optical means;
   polychromator means;
   second optical means for sequentially directing said reference beam and a reflected image of a substantial portion of said illuminated sample area towards said polychromator, the reflection angle between said illumination directed toward said sample and said reflected sample image being relatively small, said relatively large illuminated sample and reflected image areas and said small reflection angle providing a large depth of field;
   third optical means disposed in the optical path between said second optical means and said polychromator means to focus the light directed from said second optical means onto said polychromator means; and
   analyzing means connected to said polychromator means to analyze said reference beam and said reflected sample image over a range of wavelengths to determine the spectral characteristics of the sample.

2. The remote reading spectrophotometer according to claim 1, wherein said analyzing means further comprise a computer.

3. The remote reading spectrophotometer according to claim 1 wherein said polychromator means further comprise a separation filter to separate the light incident thereon into component wavelengths and detection means for detecting the intensity of light at each said component wavelength.

4. The remote reading spectrophotometer according to claim 1 wherein said illumination means further comprise a pulsed Xenon lamp.

5. The remote reading spectrophotometer according to claim 1 further comprising a curved mirror disposed behind said pulsed Xenon lamp to direct stray illumination from said lamp towards said first optical means.

6. The remote reading spectrophotometer according to claim 1 wherein said reference beam means further comprise a beamsplitter disposed in the optical path of said illumination between said aperture defining means and said objective lens means.

7. The remote reading spectrophotometer according to claim 6 further comprising an integrating sphere having a first aperture therein to receive said reference beam from said beamsplitter.

8. The remote reading spectrophotometer according to claim 7 wherein said integrating sphere further includes a second entrance aperture and third exit aperture opposed to one another along a chord through said sphere such that the optical path of said reflected sample image passes directly through said integrating sphere.

9. The remote reading spectrophotometer according to claim 8 wherein said second optical means further comprise a beamswitch disposed adjacent to said third exit aperture, said beamswitch permitting the integrated reference beam from said integrating sphere and said reflected sample image to be sequentially focused onto said polychromator by said third optical means.

10. The remote reading spectrophotometer according to claim 1 wherein said second optical means further comprise a beamswitch.

11. The remote reading spectrophotometer according to claim 9 further comprising optical monitoring means disposed within said integrating sphere for continuously detecting and monitoring said integrated reference beam at at least one wavelength as both said reference beam and said reflected sample image are sequentially directed towards said polychromator.

12. The remote reading spectrophotometer according to claim 1 further comprising scanning means for successively directing said illumination beam from said first optical means onto successive portions of the distant sample, said scanning means receiving said reflected image from said distant sample and directing said reflected image to said second optical means.

13. The remote reading spectrophotometer according to claim 12 wherein said scanning means further comprise a plane scanning mirror.

14. The spectrophotometer according to claim 12 wherein said scanning means provides a raster scan.

15. The remote reading spectrophotometer according to claim 1 wherein said objective lens means transmits said illumination to the sample in a substantially collimated beam.

16. The remote reading spectrophotometer according to claim 1 wherein said reflection angle is substantially zero.

17. A spectrophotometer for measuring a distant sample comprising
   a high intensity pulsed Xenon illumination source;
   condenser lens means for receiving illumination from said illumination source and transmitting said illumination;
   aperture defining means in the optical path of said illumination transmitted by said condenser lens means;
   illumination lens means for uniformly illuminating an area of a distant sample to be measured by projecting an image of said illumination from said aperture defining means onto said sample area;
   reference beam means disposed in the optical path of said illumination between said aperture defining means and said illumination lens means for obtaining an illumination reference beam;
   polychromator means;
   image directing optical means for sequentially directing said reference beam and a reflected image of a substantial portion of said illuminated sample area towards said polychromator, the reflection angle between said illumination directed toward said sample and said reflected sample image being relatively small, said relatively large illuminated sample and reflected image areas and said small reflection angle providing a large depth of field;
   image focusing optical means disposed in the optical path between said image directing optical means and said polychromator means for focusing light directed from said image directing optical means onto said polychromator means, said image focusing optical means effectively averaging said reflected image of said uniformly illuminated sample area;
   analyzing means connected to said polychromator means for analyzing said reference beam and said reflected sample image over a range of wavelengths to determine the spectral characteristics of the sample.

18. The spectrophotometer according to claim 17 wherein said illumination lens means transmits said illumination to the distant sample in a substantially collimated beam.

19. The spectrophotometer according to claim 17 wherein said reflection angle is substantially zero.

20. The spectrophotometer according to claim 17 wherein said reference beam means further comprise a beamsplitter disposed in the optical path of said illumination between said aperture defining means and said illumination lens means.

21. The spectrophotometer according to claim 20 further comprising an integrating sphere having a first aperture therein to receive said reference beam from said beamsplitter.

22. The spectrophotometer according to claim 21 wherein said integrating sphere further includes a second entrance aperture and third exit aperture opposed to one another along a chord through said sphere such that the optical path of said reflected sample image passes directly through said integrating sphere.

23. The spectrophotometer according to claim 22 wherein said image directing optical means further comprise a beamswitch disposed adjacent to said third exit aperture, said beamswitch permitting the integrated reference beam from said integrating sphere and said reflected sample image to be sequentially focused onto said polychromator by said image focusing optical means.

24. The spectrophotometer according to claim 23 further comprising optical monitoring means disposed within said integrating sphere for continuously detecting and monitoring said integrated reference beam at at least one wavelength as both said reference beam and said reflected sample image are sequentially directed towards said polychromator.

25. The spectrophotometer acording to claim 17 further comprising scanning means for successively directing said illumination image from said illumination lens means onto successive portions of the distant sample, said scanning means receiving said reflected image from the distant sample and directing said reflected image to said image directing optical means.

26. The spectrophotometer according to claim 25 wherein said scanning means further comprise a plane scanning mirror.

27. The spectrophotometer according to claim 17 wherein said analyzing means further comprise a computer.

* * * * *